(12) United States Patent
Chakravarthy et al.

(10) Patent No.: US 9,636,069 B2
(45) Date of Patent: May 2, 2017

(54) SYSTEM AND METHOD FOR MONITORING AND CLASSIFYING ATRIAL FIBRILLATIONS

(71) Applicant: Medtronic Monitoring, Inc., San Jose, CA (US)

(72) Inventors: Niranjan Chakravarthy, Eden Prairie, MN (US); Abhi Chavan, Maple Grove, MN (US)

(73) Assignee: Medtronic Monitoring, Inc., San Jose, CA (US)

(*) Notice: Subject to any disclaimer, the term of this patent is extended or adjusted under 35 U.S.C. 154(b) by 116 days.

(21) Appl. No.: 14/739,399

(22) Filed: Jun. 15, 2015

(65) Prior Publication Data

US 2016/0361024 A1 Dec. 15, 2016

(51) Int. Cl.
*A61B 5/046* (2006.01)
*A61B 5/00* (2006.01)
*A61B 5/11* (2006.01)
*A61B 5/0205* (2006.01)
*A61B 5/0404* (2006.01)
*A61B 5/0408* (2006.01)

(52) U.S. Cl.
CPC .......... *A61B 5/7264* (2013.01); *A61B 5/0006* (2013.01); *A61B 5/0205* (2013.01); *A61B 5/046* (2013.01); *A61B 5/1118* (2013.01); *A61B 5/6832* (2013.01); *A61B 5/7278* (2013.01); *A61B 5/7289* (2013.01); *A61B 5/0404* (2013.01); *A61B 5/0408* (2013.01); *A61B 2562/04* (2013.01)

(58) Field of Classification Search
CPC ..... A61B 5/046; A61B 5/1118; A61B 5/7289; A61B 5/0006; A61B 5/0205; A61B 5/6832; A61B 5/7264; A61B 5/4884
See application file for complete search history.

(56) References Cited

U.S. PATENT DOCUMENTS

| 7,899,531 B1 | 3/2011 | Benser et al. |
| 2009/0076345 A1 | 3/2009 | Manicka et al. |
| 2013/0274584 A1 | 10/2013 | Finlay et al. |

OTHER PUBLICATIONS

Charkravarthy et al., "A study of activity and body posture with the PiiX mobile body adherent device", Engineering in Medicine and Biology Society, 36th Annual International Conference of the IEEE, Aug. 26-30, 2014, pp. 2714-2717.
Coumel, "Autonomic influences in atrial tachyarrhythmias", Journal of Cardiovascular Electrophysiology, vol. 7 (10), Oct. 1996, pp. 999-1007.
Gibbons et al., "ACC/AHA Guidelines for Exercise Testing: Executive Summary", Circulation, vol. 96, 1997, pp. 345-354.
(Continued)

*Primary Examiner* — Tammie K Heller
(74) *Attorney, Agent, or Firm* — Billion & Armitage; Michael A. Collins

(57) ABSTRACT

A system and method of detecting and classifying atrial fibrillations (AFs) monitors an electro-cardiogram (ECG) signal of the patient. Based on the monitored ECG signals, AF episodes are detected. Monitored physiological parameters are utilized to determine an activity level of the patient at the time of the detected AF episode, wherein the activity level is associated with the detected AF episode. The etiology of the detected AF episodes is classified as adrenergic if the AF episodes occur while the patient is active, and classified as vagal if the AF episodes occur while the patient is at rest.

15 Claims, 15 Drawing Sheets

(56) References Cited

OTHER PUBLICATIONS

Kaab, "Different types of atrial fibrillation: why they should receive different treatments", EHRA/EUROPACE, Madrid, Spain, Jun. 26-29, 2011, 32 pages.

Lombardi et al., "Heart rate variability and its sympatho-vagal modulation", Cardiovascular Research, vol. 32, 1996, pp. 208-216.

Mandyam et al., "Alcohol and Vagal Tone as Triggers for Paroxysmal Atrial Fibrillation", Am J. Cardiol., vol. 110 (3), Aug. 1, 2012, pp. 364-368.

Rosso et al., "Vagal Paroxysmal Atrial Fibrillation: Prevalence and Ablation Outcome in Patients Without Structural Heart Disease", Journal of Cardiovascular Electrophysiology, vol. 21 (5), May 2010, pp. 489-493.

Van Den Berg et al., "Analysis of heart rate variability in a patient with paroxysmal atrial fibrillation", Eur Heart J., vol. 16 (12), Dec. 1995, p. 2011.

Notification of Transmittal of the International Search Report and the Written Opinion of the International Searching Authority, or the Declaration for PCT/US2016/037355, mailed on Sep. 16, 2016.

Efremidis, et al., "The impact of bagotonic, adrenergic, and random type of paroxysmal atrial fibrillation on left atrial ablation outcomes", International Journal of Cardiology, 168, 2013, 4015-4018.

Yeh, et al., "Vagal Atrial Fibrillation", Acta Cardiol Sin, 23, 2007, 1-12.

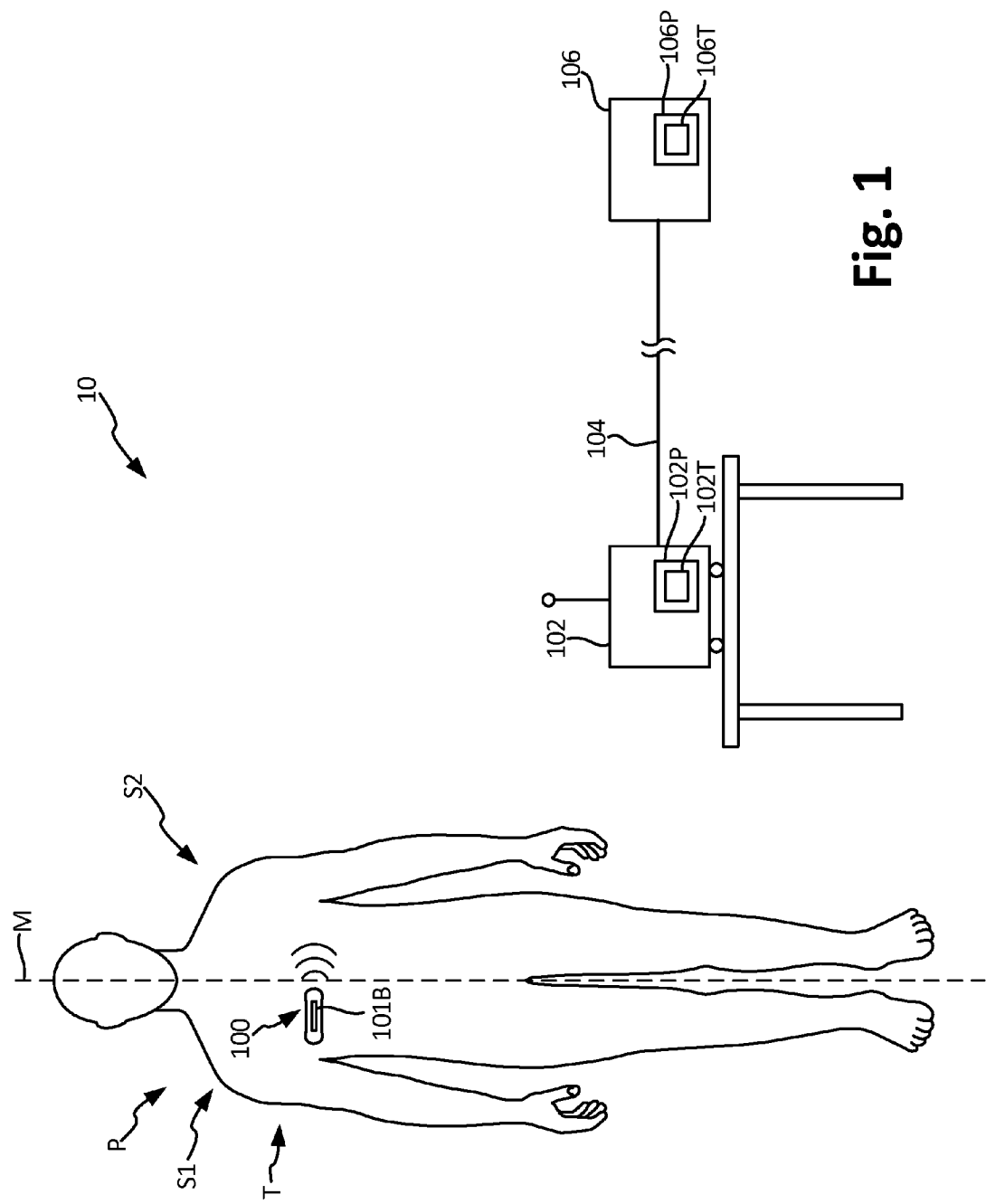

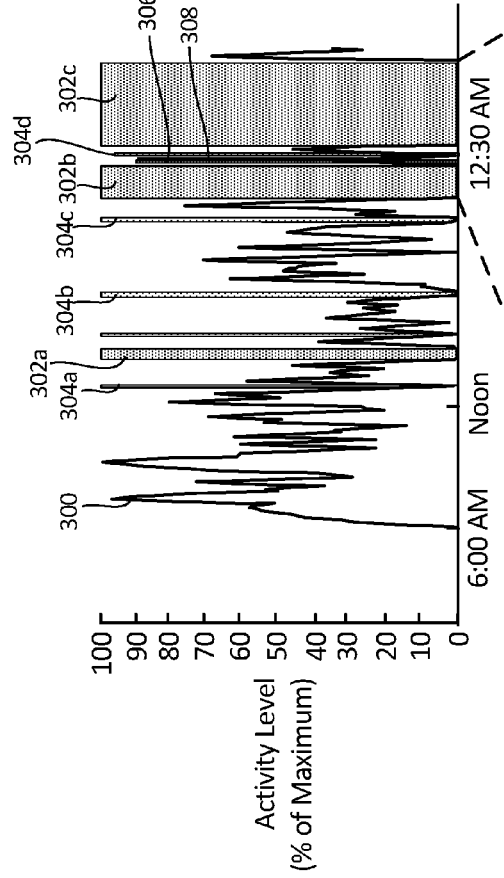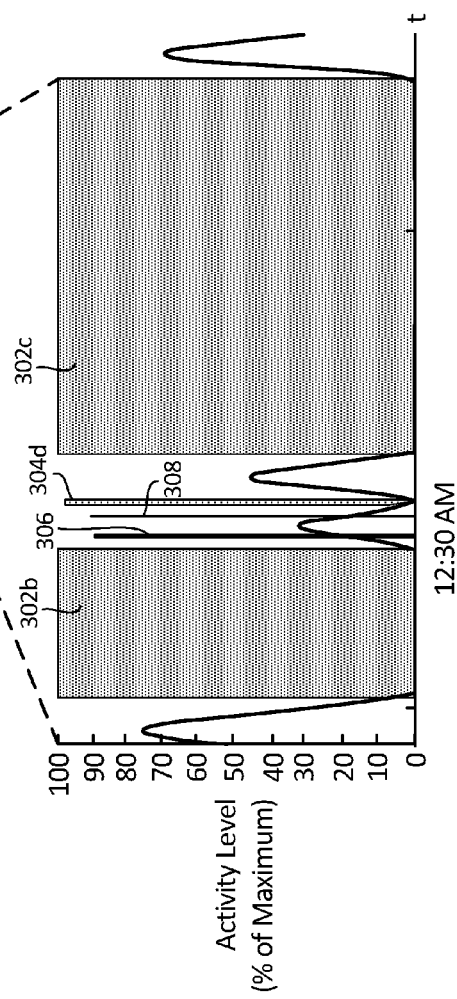

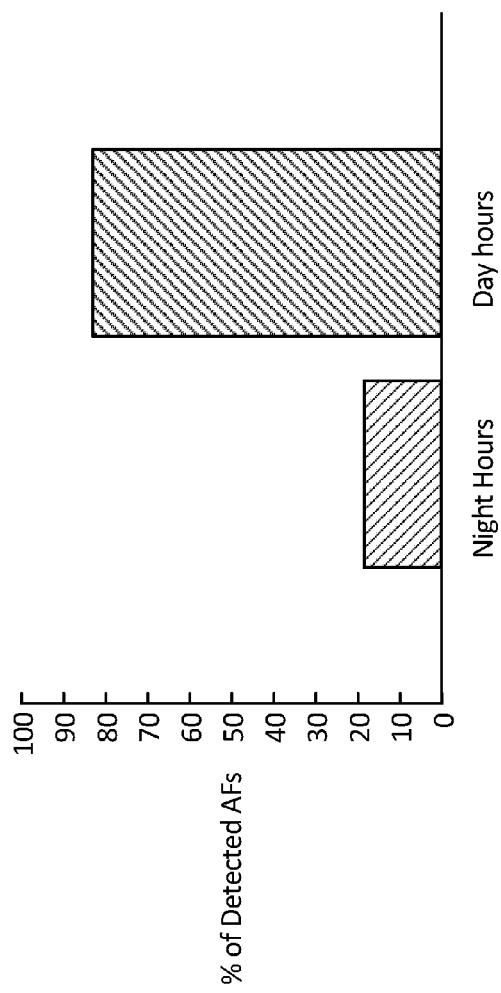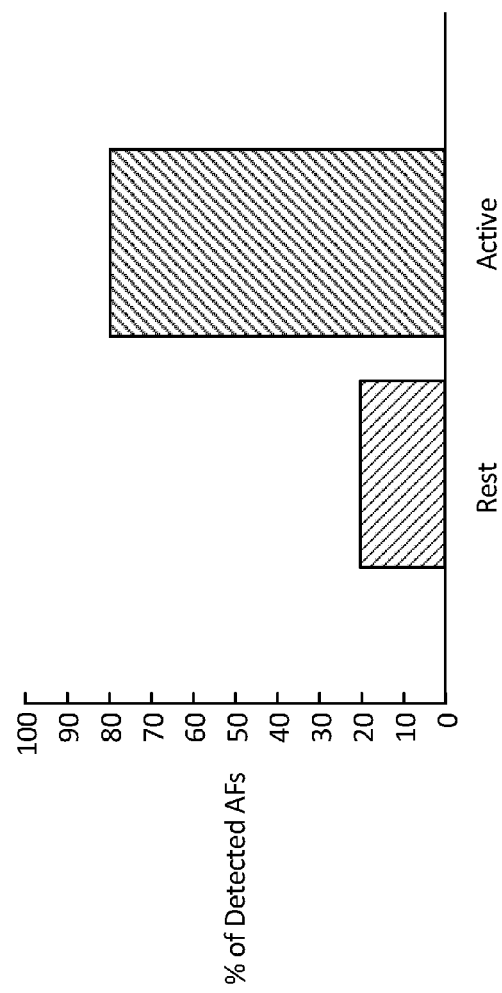

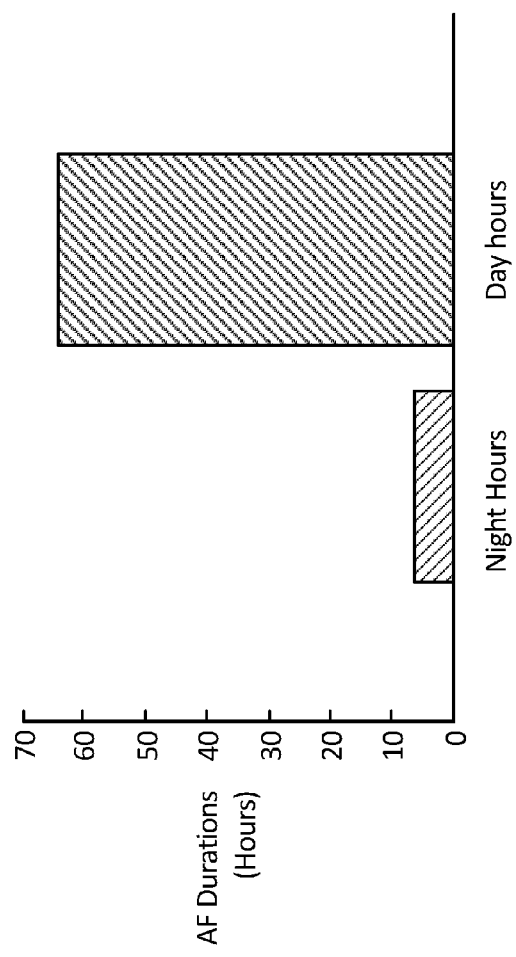
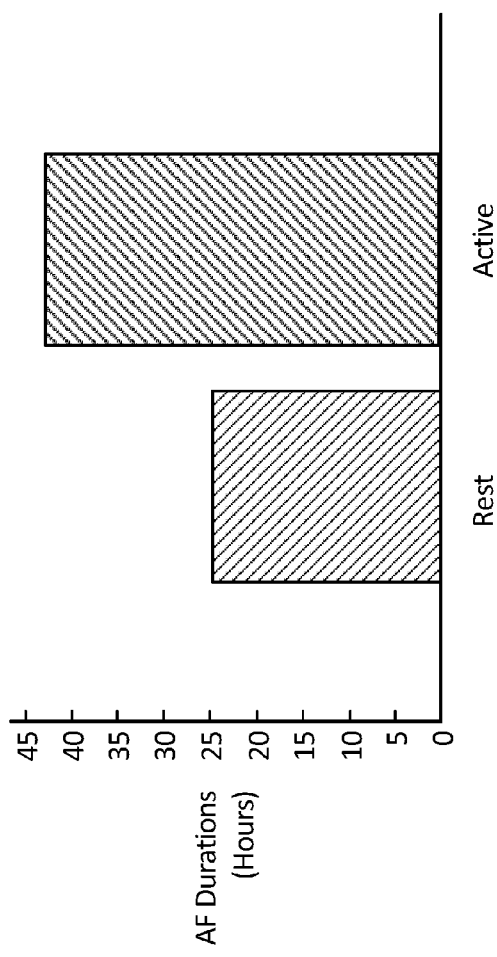
Fig. 5C
Fig. 5D

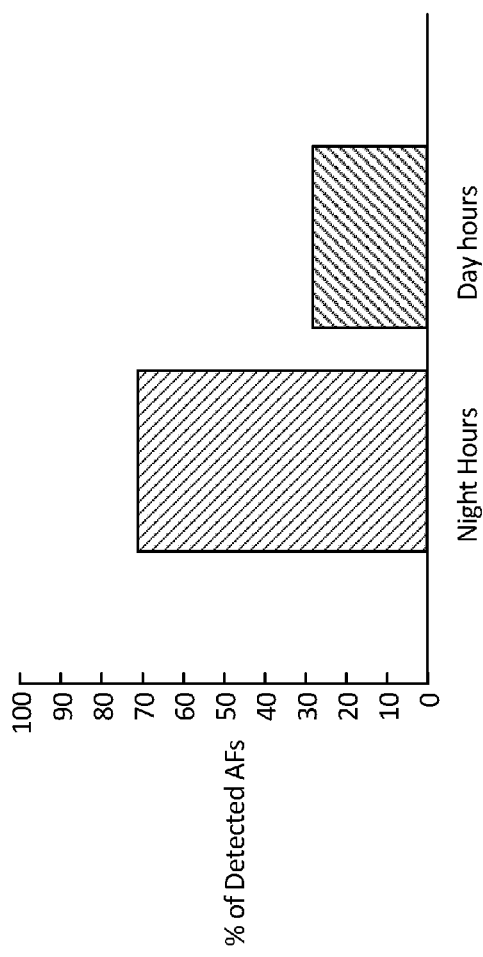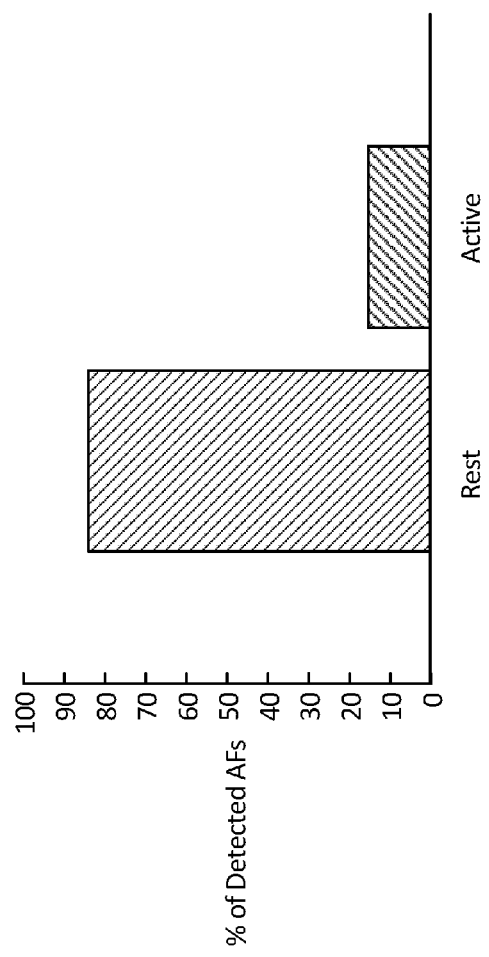

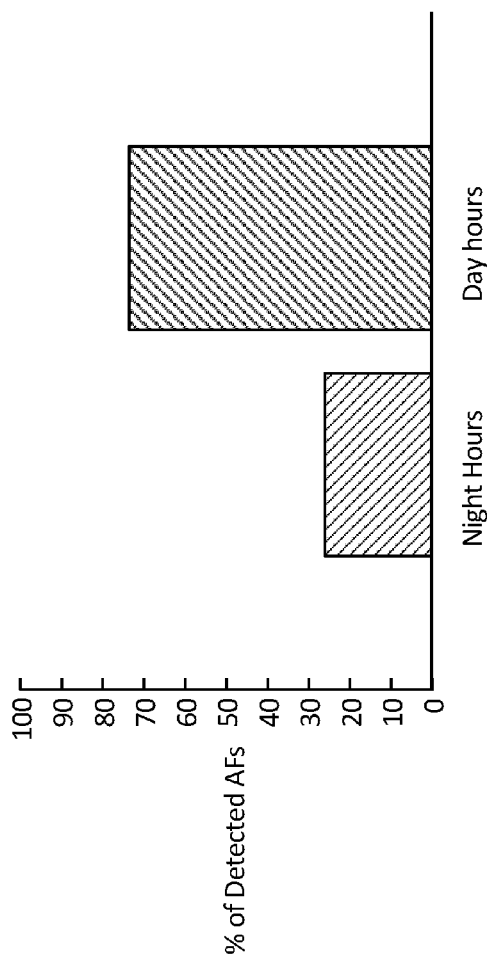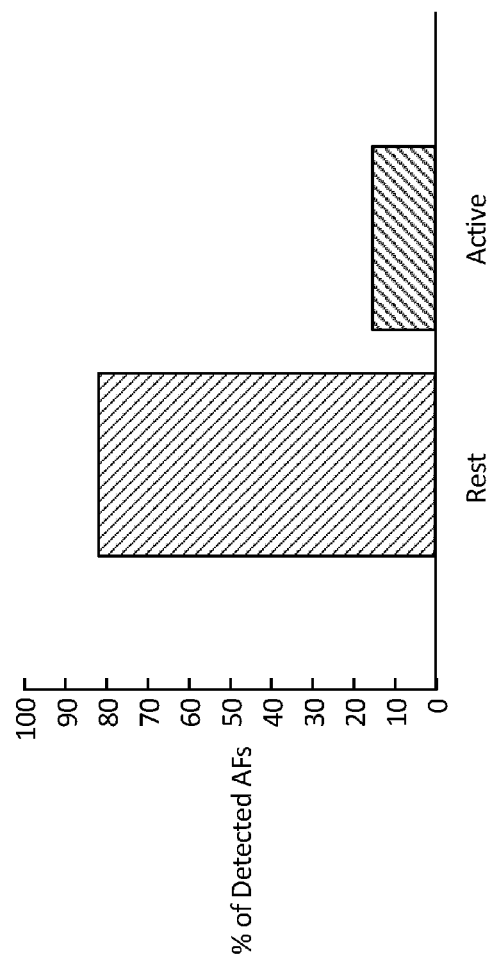

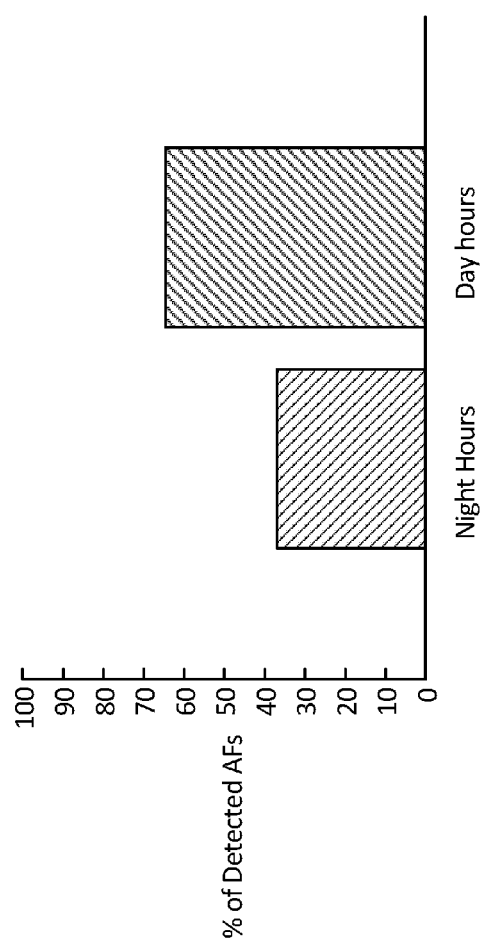
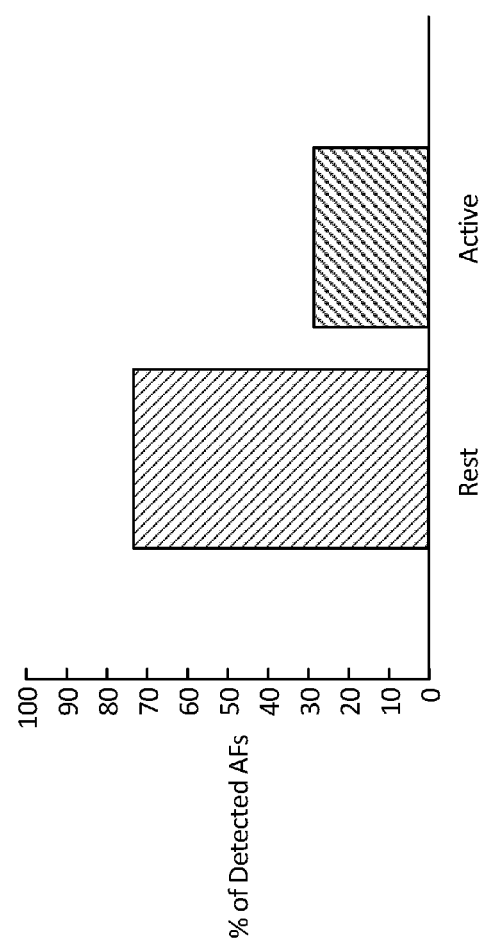

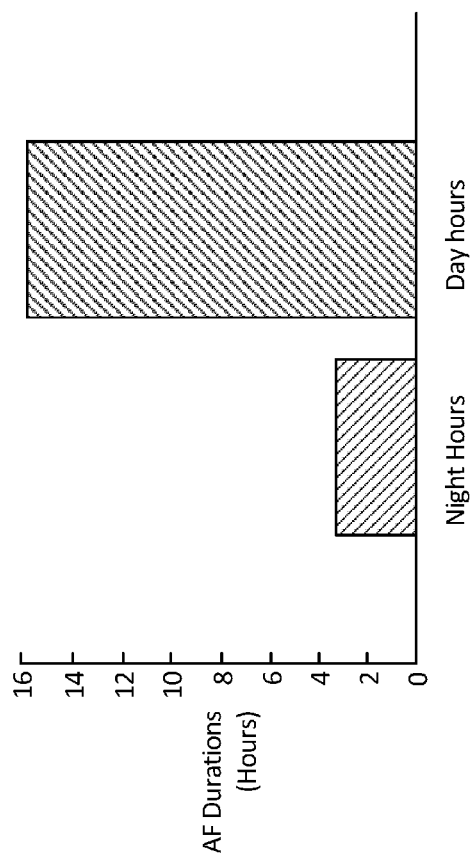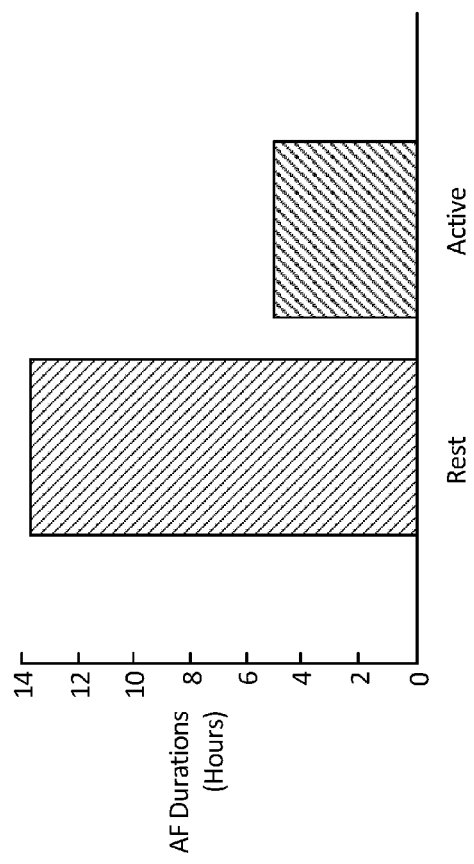

US 9,636,069 B2

SYSTEM AND METHOD FOR MONITORING AND CLASSIFYING ATRIAL FIBRILLATIONS

TECHNICAL FIELD

The present disclosure is related in general to patient monitoring and in particular to monitoring, detecting and classifying atrial fibrillations (AFs).

BACKGROUND

Atrial fibrillation (AF) is a condition that results in the irregular and oftentimes rapid beating of the heart, sometimes also referred to as an arrhythmic condition. Although AF may not in and of itself represent a threat to the health of the patient, it may represent a symptom of an underlying problem. Differentiating between different types of AF allows a physician to better diagnose and treat the underlying problem.

Atrial fibrillation is detected by monitoring the electrical signals (e.g., electrocardiogram signals) associated with the patient. Electrocardiogram signals are monitored by attaching two or more leads to the patient and monitoring the electrical response. In some cases, a physician or doctor will monitor ECG signals while putting the patient through a series of exercises such as walking on a treadmill or riding a stationary bike. The resulting ECG signal is analyzed to determine whether the patient is subject to AF. However, this requires the patient to be present in the physician's office and for the arrhythmia condition to present during the prescribed duration of the exam or test.

It would therefore be beneficial to develop a system that provides long-term monitoring and detection of AFs, which can be utilized to improve etiology of the atrial fibrillations.

SUMMARY

Described herein is a system and method of detecting and classifying atrial fibrillations (AFs). To this end, the system monitors an electro-cardiogram (ECG) signal of the patient and detects AF episodes based on the monitored ECG signals. In addition, monitored physiological parameters are utilized to determine an activity level of the patient at the time of the detected AF episode, wherein the activity level is associated with detected AF episodes. Based on a combination of the detected AF episodes and associated activity levels, the cause of the AF episodes are classified as adrenergic or vagal.

BRIEF DESCRIPTION OF THE DRAWINGS

FIG. 1 illustrates a schematic view of a monitoring and treatment system comprising a patient utilizing a medical device measuring one or more physiological values, according to an embodiment of the present invention.

FIGS. 3A-3B are charts generated as part of a monitoring report that correlates identification of arrhythmias in a patient with activity levels of the patient according to an embodiment of the present invention.

FIGS. 5A-5D are bar charts generated as part of a monitoring report that graphically illustrate the relationship between detected arrhythmias and patient state utilized to aid in determining the etiology of the detected arrhythmia according to an embodiment of the present invention.

FIGS. 6A-6D are bar charts generated as part of a monitoring report that graphically illustrate the relationship between detected arrhythmias and patient state utilized to aid in determining the etiology of the detected arrhythmia according to an embodiment of the present invention.

FIGS. 7A-7D are bar charts generated as part of a monitoring report that graphically illustrate the relationship between detected arrhythmias and patient state utilized to aid in determining the etiology of the detected arrhythmia according to an embodiment of the present invention.

FIGS. 8A-8D are bar charts generated as part of a monitoring report that graphically illustrate the relationship between detected arrhythmias and patient state utilized to aid in determining the etiology of the detected arrhythmia according to an embodiment of the present invention.

DETAILED DESCRIPTION

Figure 2A:
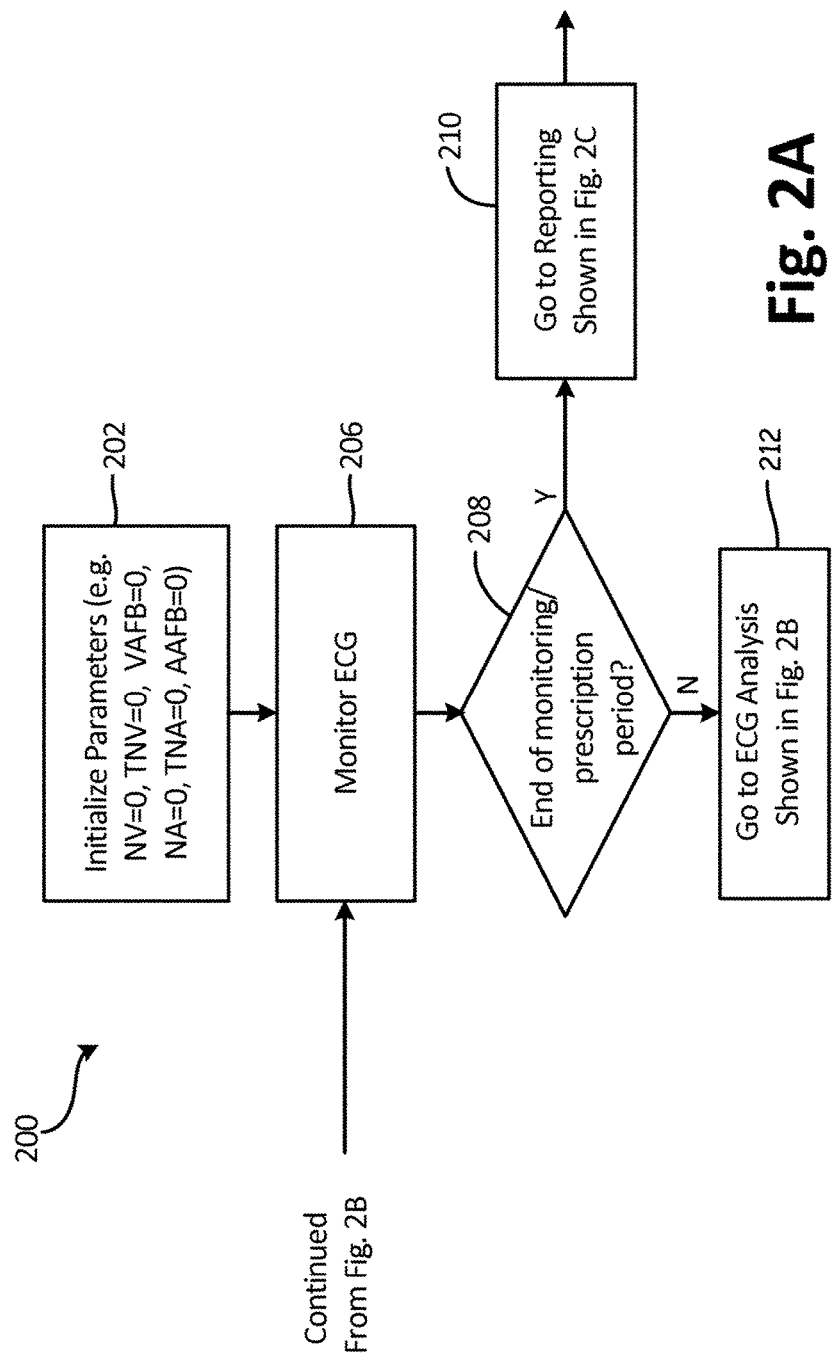
FIGS. 2A-2C are flowcharts that illustrate steps performed to differentiate between different types of arrhythmias according to an embodiment of the present invention.

The present invention is related to a system and method of monitoring and classifying arrhythmias. In particular, a patient device is utilized to monitor electrical signals from the patient (ECG) to detect atrial fibrillations. In addition, the patient device is utilized to collect one or more additional physiological parameters from the patient to determine a patient state (e.g., activity state). The etiology of the detected arrhythmias is determined based on the collected information and communicated to a physician.

A benefit of the system and method described herein, is that it does not require a patient to be present in the physician's office to collect the data. Rather, the patient wears the device for an extended period of time (e.g. monitoring period), and data is collected as the patient undergoes normal day to day activities, including periods of rest and periods of activity. In addition, the system and method described herein prevents the physician/doctor from having to review all data collected over the period of time the patient wears the adherent/implantable device. This provides considerable time-savings to health care providers, without sacrificing quality of the care provided.

FIG. 1 shows a patient P and a monitoring system 10. Patient P comprises a midline M, a first side S1, for example a right side, and a second side S2, for example a left side. Monitoring system 10 comprises a patient measurement device 100, gateway 102, and remote monitoring center 106. In the embodiment shown in FIG. 1, patient measurement device 100 (hereinafter, "adherent device 100") is an adherent device that attaches to the skin of the patient, but in other embodiments may be an implantable or injectable device. Adherent device 100 can be adhered to a patient P at many locations, for example thorax T of patient P. In many embodiments, the adherent device may adhere to one side of the patient, from which side data can be collected. A benefit of utilizing an adherent device such as adherent device 100 is that it may be utilized to collect physiological data from the patient while the patient goes about normal day-to-day activities outside of a hospital setting.

Adherent device 100 is capable of monitoring a variety of different types of data, including one or more of electrocardiogram signals (ECG), bio-impedance, respiration, heart rate, heart rhythm, heart rate variability (HRV), heart rate turbulence (HRT), heart sounds, respiratory sounds, blood pressure, activity (e.g., rest, active), posture, and wake/sleep. In one embodiment, ECG signals are utilized to automatically detect arrhythmic states. In other embodiments the patient may initiate a patient-triggered arrhythmia signal (e.g., by depressing a button or switch on adherent device 100) to trigger a patient detected arrhythmic event. As described in more detail below, additional physiological parameters are measured/monitored by adherent device 100 and utilized either alone or in combination to make determinations regarding patient state (e.g., patient motion may be monitored to determine an activity level of the patient).

Adherent device 100 can wirelessly communicate with remote center 106. The communication may occur directly (via a cellular or Wi-Fi network), or indirectly through intermediate device or gateway 102. The gateway 102 may comprise components of the zLink™, a small portable device similar to a cell phone that wirelessly transmits information received from adherent device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by expert human operators to verify accuracy. For example, ECG strips captured and communicated to remote center 106 from adherent device 100 can be adjudicated for arrhythmias by experts located at remote center 106. Communication may include physiological data monitored by adherent device 100 or may include analysis/reports generated locally by adherent device 100.

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters monitored by adherent device 100 may be analyzed by one or more of the distributed processors included as part of adherent device 100, gateway 102, and/or remote monitoring center 106.

In an exemplary embodiment, adherent device 100 may continuously monitor physiological parameters, communicate wirelessly with a remote center, and provide alerts when necessary. The adherent patch may attach to the patient's thorax and contains sensing electrodes, battery, memory, logic, and wireless communication capabilities. In on embodiment described in more detail with respect to FIGS. 2A-2C, adherent device 100 collects physiological data from the patient, some of which may be communicated to remote center 106 for verification. In addition, adherent device 100 locally processes monitored physiological data to detect, classify and generate reports related to arrhythmia etiology. One or more of the monitored physiological data and generated reports may then be communicated to remote center 106 for physician review/verification. In other embodiments, monitored data collected by adherent device 100 is communicated to remote monitoring system 106, which analyzes the data to detect, classify and generate reports related to arrhythmia etiology. A benefit of locally processing collected data (i.e., processing on adherent device 100), is that this decreases the amount of data that must be communicated to remote center 106. However, this is at the expense of requiring additional processing power located locally on adherent device 100.

Figure 2B:
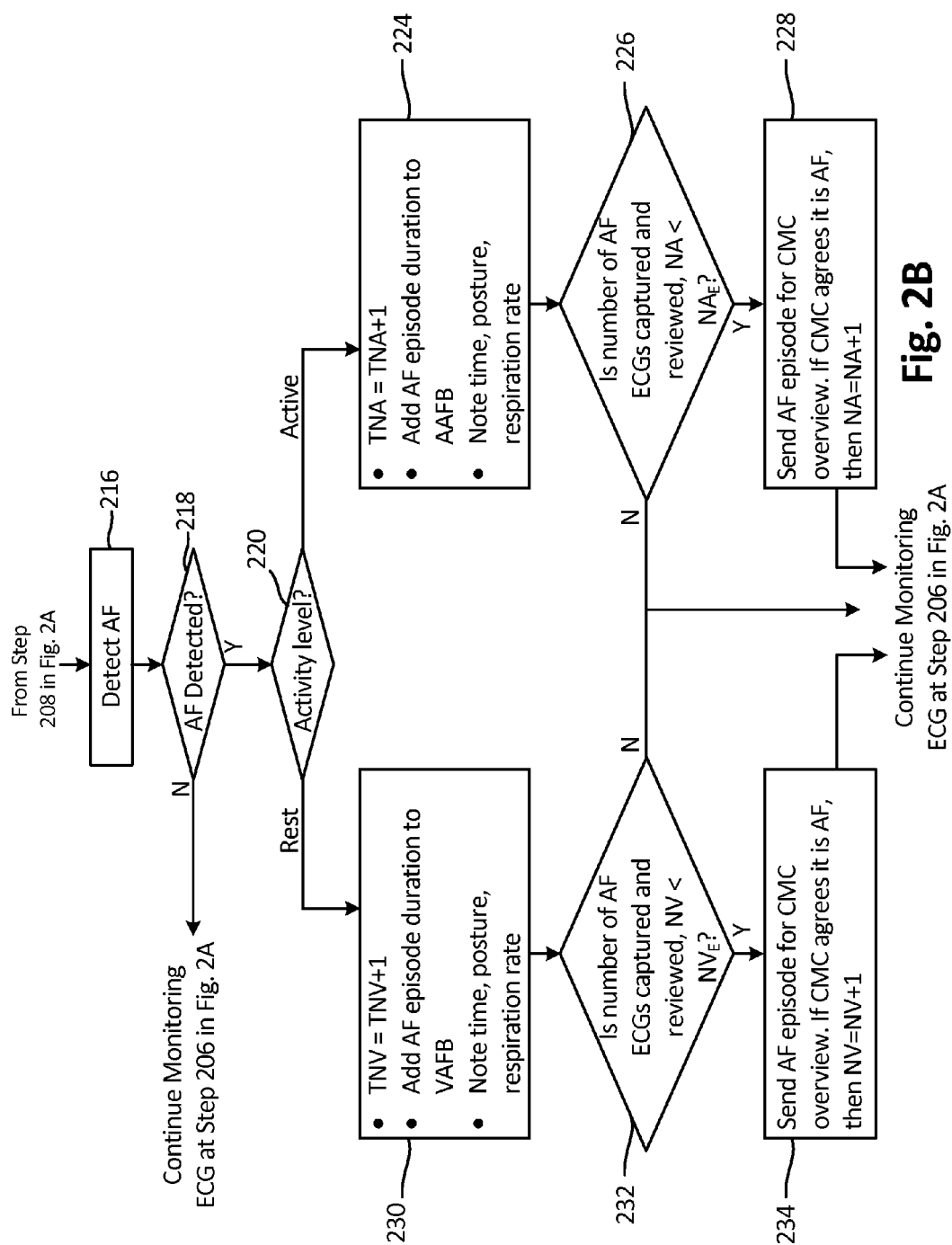
Figure 2C:
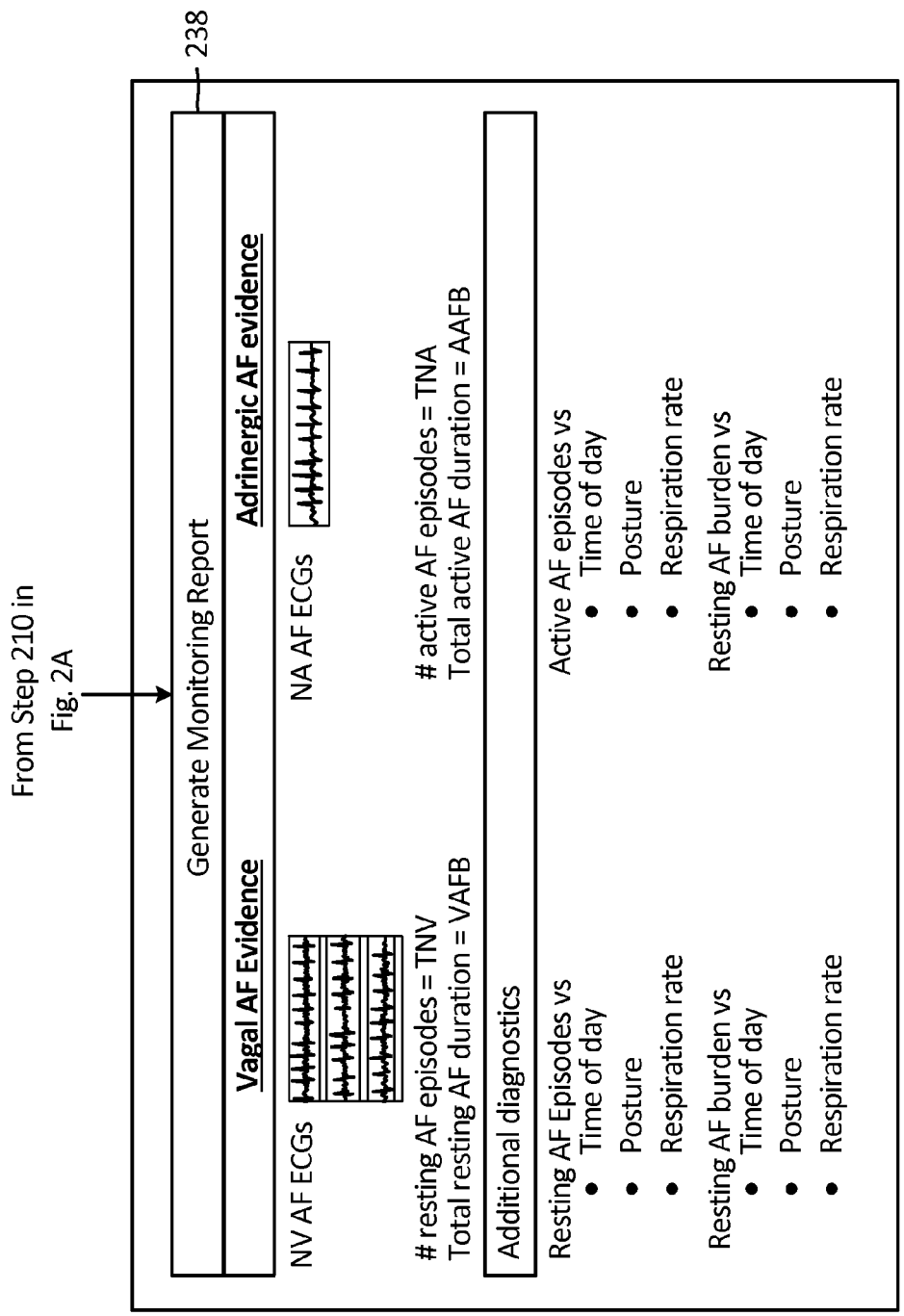

FIGS. 2A-2C are flowcharts that illustrate steps performed to differentiate between types of arrhythmias according to an embodiment of the present invention. In particular, the embodiment shown in FIGS. 3A-3C illustrate analysis of physiologic data collected from a patient to differentiate between vagal atrial fibrillation (AF) and adrenergic AF.

At step 202, prior to beginning the analysis of collected or soon to be collected physiological data, a number of variables are initialized. In the embodiment shown in FIG. 2A, variables include a count of resting AF ECG strips indicative of vagal AF included in final report (NV); total number of resting AF episodes indicative of vagal AF in the monitoring period (TNV); total resting AF burden/duration indicative of vagal AF in monitoring period (VAFB); number of active AF ECG strips indicative of adrinergic AF included final report (NA); total number of active AF episodes indicative of adrenergic AF in the monitoring period (TNA); and total active AF burden/duration indicative of adrenergic AF in the monitoring period (AAFB). In the embodiment shown in FIG. 2A, each of these values is initialized to zero, although in other embodiments initialization may be provided at different values. In addition, the variable $NV_E$ describes the number of resting AF ECG strips to be collected in the final report and $NA_E$ describes the number of active AF ECG strips to be collected in the final report. These are maximum values that may be selectively determined by a physician or user to dictate how many AF ECG strips are recorded and provided for analysis. In many embodiments, while the patient may experience tens or hundreds of AF events, it is only beneficial to provide a subset of those events to the physician for review. With these variables the physician may determine the number of AF events needed for review.

At step 206, the monitoring procedure begins and/or continues, with electrocardiogram (ECG) signals being monitored by adherent/implantable device 100. Monitoring of ECG signals at step 206 may begin following the initiation step described with respect to step 202, or in response to a previous monitoring period ending as described below.

At step 208, a determination is made whether the monitoring period has ended. The monitoring period may be defined as period of time (e.g., days, weeks), or may be defined by the operability of the adherent/implantable device. For example, if it is detected that the adherent device is no longer adhered to the patient, then the monitoring period may also be terminated. If the monitoring period has ended, then the analysis continues at step 210 with reporting of the results—described in more detail with respect to FIG. 2C. If it is determined at step 208 that the monitoring period has not yet ended, then the process continues at step 212 with analysis of the monitored ECG signal, shown in FIG. 2B.

As shown in FIG. 2B, if the monitoring period has not ended, then at step 216 the monitored ECG signal is analyzed to detect atrial fibrillation. A number of well-known algorithms may be utilized to detect the presence of AF in a patient based on a measured ECG of the patient. In general, an AF event is characterized by rapid and irregular beating, although may not be accompanied by any external symptoms of the patient (e.g., no evidence of fainting, shortness of breath, or chest pain).

At step 218 a determination is made regarding whether AF was detected. If no AF was detected at step 216 then the process continues at step 206—shown in FIG. 2A—in which adherent/implantable device 100 continues monitoring the ECG signal. If AF is detected at step 218, then at step 220 the activity level of the patient is reviewed. In particular, in the embodiment shown in FIG. 2B, at step 220 a determination is made regarding the activity level of the patient. The determination regarding the activity level of the patient may be based on one or more physiological values monitored by the adherent/implantable device. For example, activity sensor and activity circuitry included as part of adherent device 100 may be used to collect physiological signals related to the activity level of the patient, wherein activity sensors may include one or more of ball switch, accelerometer, minute ventilation, HR, bioimpedance noise, skin temperature/heat flux, BP, muscle noise, posture. In other embodiments, various other physiological parameters may utilized in conjunction with physiological parameters monitored by activity sensor and circuitry, such as heart rate, respiration rate, etc. The activity threshold utilized to determine whether a patient is in an active state or a rest state may be based on one or more of the monitored physiological values, and may utilize a patient dependent threshold.

If at step 220 it is determined that the patient is in an active state, then at step 224 a total count of active AF episodes detected is incremented as illustrated by the equation (TNA=TNA+1). In addition at step 224, the AF episode duration is added to the total active AF burden/duration within the monitoring period. In one embodiment this includes determining the length of time the AF episode persists (e.g., end time—start time), and adding the measured length of time to a total duration of AF episodes measured while the patient is in an active state. In addition to incrementing/modifying variables related to AFs detected during an active patient state, physiologic data measured during the detected AF is recorded, including ECG data related to the detected AF, time of day information, posture data, respiration rate data, and or other data related to patient state at the time of the detected AF. This data may be stored locally, or may be communicated from adherent/implantable device 100 to gateway 102 and/or to remote center 106.

At step 226, a determination is made whether the number of active AF ECGs captured and reviewed is less than a maximum number of active AF ECG strips included in the final report. If the number of active AF ECGs captures is less than the maximum number of active AF ECGs allowed in the final report, then data—including ECG data—from the detected AF event is communicated to gateway 102 or remote center 106 for review by a physician for verification of a detected AF event at step 226. If the physician or reviewing party at gateway 102 or remote center 106 agrees with the initial assessment of the event as an AF event, then the total number of detected active AFs indicative of adrenergic AF is incremented (NA=NA+1) and the monitoring process continues at step 206—shown in FIG. 2A. If the physician does not agree with the AF assessment, then the total number of detected active AFs is remained unchanged and the monitoring process still continues at step 236. When the total number of detected active AFs indicative of adrenergic AF is incremented to the point that the number is greater than the threshold number of active AF episodes allowed for inclusion in the final report (e.g., NA<$NA_E$), then captured ECGs are no longer sent to remote center 106 for review at step 228. Detection of AFs and incrementing of the total number of AFs indicative of adrenergic AF (TNA) are still incremented, but captured ECGs are no longer communicated to a physician at remote center 106 for review because the desired number of active AF episodes in a monitoring period has already been reached. The monitoring process then continues at step 206.

If at step 220 it is determined that the patient is in an passive or rest state, then at step 230 a total count of resting AF episodes detected is incremented as illustrated by the equation (TNV=TNV+1). In addition at step 224, the AF episode duration is added to the total resting AF burden/duration within the monitoring period. In one embodiment this includes determining the length of time the AF episode persists (e.g., end time–start time), and adding the measured length of time to a total duration of AF episodes measured while the patient is in a rest state. In addition to incrementing/modifying variables related to AFs detected during a resting patient state, physiologic data measured during the detected AF is recorded, including ECG data related to the detected AF, time of day information, posture data, respiration rate data, and or other data related to patient state at the time of the detected AF. This data may be stored locally, or may be communicated from adherent/implantable device 100 to gateway 102 and/or to remote center 106.

At step 232, a determination is made whether the number of resting AF ECGs captured and reviewed is less than a maximum number of resting AF ECG strips included in the final report. If the number of resting AF ECGs captured is less than the maximum number of resting AF ECGs allowed in the final report, then data—including ECG data—from the detected AF event is communicated to gateway 102 or remote center 106 for review by a physician for verification of a detected AF event at step 234. If the physician or reviewing party at gateway 102 or remote center 106 agrees with the initial assessment of the event as an AF event, then the total number of detected resting AFs indicative of vagal AF is incremented (NV=NV+1) and the monitoring process continues at step 206—shown in FIG. 2A. If the physician does not agree with the AF assessment, then the total number of detected resting AFs is remained unchanged and the monitoring process continues at step 206. When the total number of detected active AFs indicative of vagal AF is incremented to the point that the number is greater than the threshold number of resting AF episodes allowed for inclusion in the final report (e.g., NV<$NV_E$), then captured ECGs are no longer sent to remote center 106 for review at step 234. Detection of AFs and incrementing of the total number of AFs indicative of vagal AF (TNV) are still incremented, but captured ECGs are no longer communicated to a physician at remote center 106 for review because the desired number of resting AF episodes in a monitoring period has already been reached. The monitoring process then continues at step 206, as shown in FIG. 2A.

When the monitoring period ends at step 208 (shown in FIG. 2A), then reporting of the events is initiated at step 210. An exemplary report generated as part of the reporting step is illustrated in FIG. 2C. In general, the purpose of the report is to provide the physician or reviewer with a snapshot of information useful in determining the etiology of arrhythmic conditions, without requiring the physician to review all monitored ECG data. Benefits of this approach include a reduction in the total amount of data communicated from adherent device 100 to remote center 106, and a reduction in the amount of data the physician must review, thereby decreasing the amount of physician time required.

In the embodiment shown in FIG. 2C, the final report includes vagal AF evidence and adrenergic AF evidence. With respect to vagal AF evidence, the data displayed to the physician includes resting AF episodes captured prior to exceeding the maximum number of resting AF episodes to be included in the final report. For example, if a maximum of three resting AF ECG strips are allowed, and three or more incidences of resting AF episodes were detected and captured, then the physician would be presented with three resting AF ECG strips. If, on the other hand, only one episode of resting AF was detected, then the physician would only be presented with a single resting AF ECG strip. In addition to ECG strips captured during the monitoring process, the report also includes a count of the total number of resting AF episodes detected (e.g., TNV). The total number of resting AF episodes detected indicates the total number of AF episodes detected while the patient was in a rest state, regardless of whether an ECG was captured and presented to the physician. In this way, the total number of AF episodes detected while the patient is at rest (TNV) may be greater than the number of vagal AF ECGs displayed. In addition, the report may also include the total resting AF duration or resting AF burden (VAFB) indicating the total amount of time the patient spend in a resting AF state.

In addition to collected AF information, the monitoring report may provide the physician with other monitored physiological data monitored with respect to the patient. In particular, the report includes graphical displays relating/correlating detected resting AF episodes with other parameters, such as time of day, patient posture, and patient respiration rate. Similarly, resting AF burden or total time spent in a resting AF state may be correlated with monitored data including time of day, posture, and/or respiration.

Similarly, with respect to adrenergic AF evidence the data displayed to the physician includes active AF episodes captured prior to exceeding the maximum number of active AF episodes to be included in the final report. As described with respect to resting AF, the number of active AF ECGs displayed is limited by the total number of active AF ECG strips allowed. For example, if a maximum of three active AF ECG strips are allowed, and three or more incidences of active AF episodes were detected and captured, then the physician would be presented with three active AF ECG strips. However, in the embodiment shown in FIG. 2C, only one active AF episode was detected, and therefore only the one captured active AF ECG strip is displayed to the physician for review. In addition to ECG strips captured during the monitoring process, the report also includes a count of the total number of active AF episodes detected (e.g., TNV). The total number of active AF episodes detected indicates the total number of AF episodes detected while the patient was in an active state, regardless of whether an ECG was captured and presented to the physician. In this way, the total number of AF episodes detected while the patient is active (TNA) may be greater than the number of adrenergic AF ECGs displayed. In addition, the report may also include the total active AF duration or active AF burden (AAFB) indicating the total amount of time the patient spend in an active AF state.

In addition to collected AF information, the monitoring report may provide the physician with other monitored physiological data monitored with respect to the patient. In particular, the report includes graphical displays relating/correlating detected active AF episodes with other parameters, such as time of day, patient posture, and patient respiration rate. Similarly, active AF burden or total time spent in an active AF state may be correlated with monitored data including time of day, posture, and/or respiration. The monitoring report may provide a diagnosis for the physician to review, or may provide only the collected data without a diagnosis.

FIGS. 3A-3B are charts that illustrate a combination of data utilized to determine the etiology of detected arrhythmias according to an embodiment of the present invention. FIG. 3A illustrates data collected over a 24 hour period, while FIG. 3B provides a zoomed-in view of data displayed with respect to FIG. 3A to illustrate detection of an AF event. In particular, charts shown in FIGS. 3A-3B may be representative of charts included as part of the monitoring report provided to the physician for review, which may be in addition to other relevant information such as ECG AF strips and other collected physiological data.

In the embodiment shown in FIGS. 3A-3B, the y-axis represents a percentage of maximum activity level on a scale of 0-100 percent, while the x-axis represents time. Solid line 300 shown in FIGS. 3A-3B represents activity level of the patient as a percentage of a maximum activity level. Shaded regions 302a, 302b, and 302c represent supine rest durations as determined from one or more sensors monitoring posture and activity level of the patient, while shaded regions 304a, 304b, 304c and 304d represent upright rest durations as determined from one or more sensors monitoring posture and activity level of the patient. Dashed line 306 indicates an auto-trigger arrhythmic event detected by adherent/implantable device 100, while dotted line 308 indicates a patient-trigger arrhythmic event.

In the embodiment shown in FIGS. 3A and 3B, an arrhythmic event occurs just after midnight while the patient was resting/asleep in a supine position. FIG. 3B illustrates a zoomed in view of the arrhythmic event occurrence detected just after midnight. As shown in FIG. 3B, the patient is in a supine rest state as indicated by shaded region 304b prior to the arrhythmic (AF) event. An auto-triggered arrhythmic (AF) event is detected at approximately 12:30 AM as indicated by dashed line 306, and shortly thereafter the patient gets up—as indicated by the increased activity level—and indicates a patient trigger event (e.g., by pushing a button to indicate a patient detected event). Shortly thereafter, the patient returns to a supine rest state as indicated by shaded region 304c.

Assuming that the maximum number of ECG AF strips has not yet been reached, the AF event triggered and recorded at approximately 12:30 AM may be communicated from adherent/implantable device 100 to gateway 102 and/or remote center 106, where the AF event is verified by a physician/attendant. Assuming the event is verified as an AF event, the ECG AF strip is stored and provided as part of the report provided to the physician at the end of the monitoring period along with the charts shown in FIGS. 3A-3B. In this case, assuming no other AF events are detected—or assuming that subsequent AF events occur under similar patient circumstances (e.g., AF occurs while at rest, supine, etc.)—then a diagnosis may be generated either locally by adherent/implantable device 100 or remotely at remote center 106. The diagnosis is based on the AF events detected—including number of AF events and AF duration/burden—in combination with the activity level of the patient at the time of each AF event. For example, in the embodiment shown in FIGS. 3A-3B, an AF event is detected while the patient was in a supine, rest state. In response, the diagnosis indicates cholinergic AF, which is verified by the physician/doctor via review of data provided as part of the monitoring report.

Figures 4A, 4B:
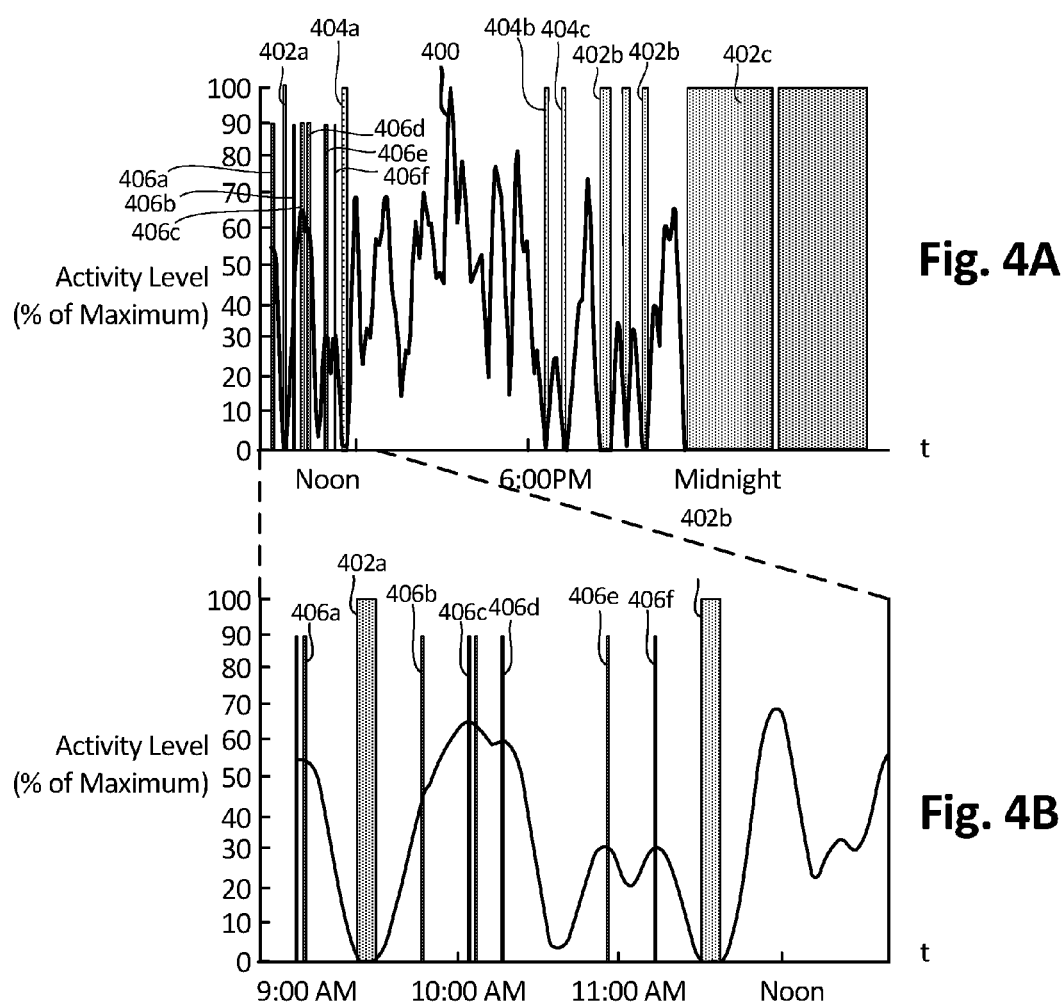
FIGS. 4A-4B are charts generated as part of a monitoring report that graphically correlate the identification of arrhythmias in a patient with activity levels of the patient according to an embodiment of the present invention.

FIGS. 4A-4B are charts that illustrate a combination of data utilized to determine the etiology of detected arrhythmias according to an embodiment of the present invention. Once again, FIG. 4A illustrates data collected over a 24-hour period, while FIG. 4B zooms in on a portion of the data shown in FIG. 4A.

In the embodiment shown in FIGS. 4A-4B, the y-axis represents a percentage of maximum activity level on a scale of 0-100 percent, while the x-axis represents time. Solid line 400 shown in FIGS. 4A-4B represents activity level of the patient as a percentage of a maximum activity level. Shaded regions 402a, 402b, 402c, and 402d represent supine rest durations as determined from one or more sensors monitoring posture and activity level of the patient, while shaded regions 404a, 404b, and 404c represent upright rest durations as determined from one or more sensors monitoring posture and activity level of the patient. Dashed vertical lines 406a, 406b, 406c, 406d, 406e, and 406f indicate an auto-trigger arrhythmic event detected by adherent/implantable device 100. No patient-trigger arrhythmic events are shown in FIGS. 4A and 4B. As discussed with respect to FIGS. 3A-3B, depending on the number of ECG AF strips that have been collected, detected auto-trigger arrhythmic events 406a-406f may be sent to gateway 102 and/or remote center 106 for verification of an arrhythmic event by a physician. If verified as an arrhythmic event, the ECG AF strip is stored and provided as part of the monitoring report delivered at the end of the monitoring period along with other collected information, such as the charts shown in FIGS. 4A-4B.

As illustrated in FIG. 4B, auto-trigger arrhythmic events 406a-406f were detected during periods of patient activity. In one embodiment of the present invention, in response to the combination of detected arrhythmias and activity level of the patient during the arrhythmic events, a diagnosis is generated—either locally on adherent/implantable device 100 or remotely at remote center 106—indicating adrenergic AF. In other embodiments, no diagnosis is generated either locally or remotely, but rather the report is provided to the physician that includes data relevant to determining the etiology of the AF, such as the graphs shown in FIGS. 4A-4B indicating the number of AF occurrences while the patient is in an active state.

FIGS. 5A-5D are bar charts provided as an output to a physician/doctor that illustrates graphically relationships between detected arrhythmias and patient state utilized to determine the etiology of the detected arrhythmia according to an embodiment of the present invention. One or more of the charts relating monitored AF events and durations to time of day and activity level may be presented to the physician for review or utilized in generating a diagnosis. In particular, FIG. 5A is a bar chart that relates total number of detected arrhythmic events to time of day (i.e., nighttime hours, daytime hours). FIG. 5B is a bar chart that relates total number of detected arrhythmic events to activity level of the patient (i.e., at rest or active). FIG. 5C relates AF burden within the prescription period to time of day, and FIG. 5D relates AF burden within the prescription period to activity level of the patient (i.e., at rest or active). In one embodiment, the instances of AF events and AF burden described with FIGS. 5A-5D represent those AF episodes that are transmitted by adherent/implantable device 100 to remote center 106 and corroborated by a physician/technician.

In the embodiment shown in FIG. 5A, the percentage of detected AF episodes occurring at night (between the hours of 10:00 PM and 8:00 AM) is approximately eighteen, while the percentage of AF episodes occurring during the day (between the hours of 8:00 AM and 10:00 PM) is approximately eighty-two. In addition, FIG. 5B indicates that the percentage of detected AF episodes detected during periods of rest is approximately twenty, while the percentage of detected AF episodes detected during periods of activity is approximately eighty. The embodiment shown in FIG. 5C illustrates that the measured AF event durations (measured in hours) occurring at night is approximately eight hours, while the measured AF event durations occurring during the day is approximately sixty hours. FIG. 5D illustrates that the measured AF event duration occurring during periods of rest is approximately twenty-five hours while the measured AF event duration occurring during periods of activity is approximately forty-two hours.

Based on the information provided in FIGS. 5A-5D, which indicates that for this patient most occurrences of AF happen during the day, while the patient is active, indicates that the etiology of the AF is likely adrenergic. This diagnosis may be provided directly to the physician for review and verification, or may be left entirely for the physician to diagnose based on the information provided and displayed. A benefit of the present invention is that not only does it allow long-term monitoring and data collection of data related to AF, but also reduces the amount of data a physician must sort through in able to make a diagnosis or verify that an automated diagnosis is accurate.

FIGS. 6A-6D are bar charts provided as an output to a physician/doctor that illustrates graphically relationships between detected arrhythmias and patient state utilized to determine the etiology of the detected arrhythmia according to an embodiment of the present invention. The bar charts shown in FIGS. 6A-6D are organized the same way as the bar charts shown in FIGS. 5A-5D, but are based on different data collected with respect to a different patient.

Figure 6C:
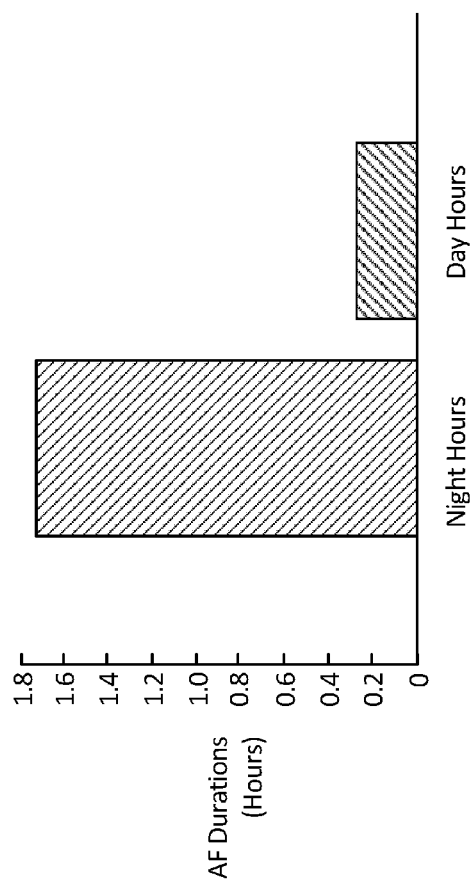
Figure 6D:
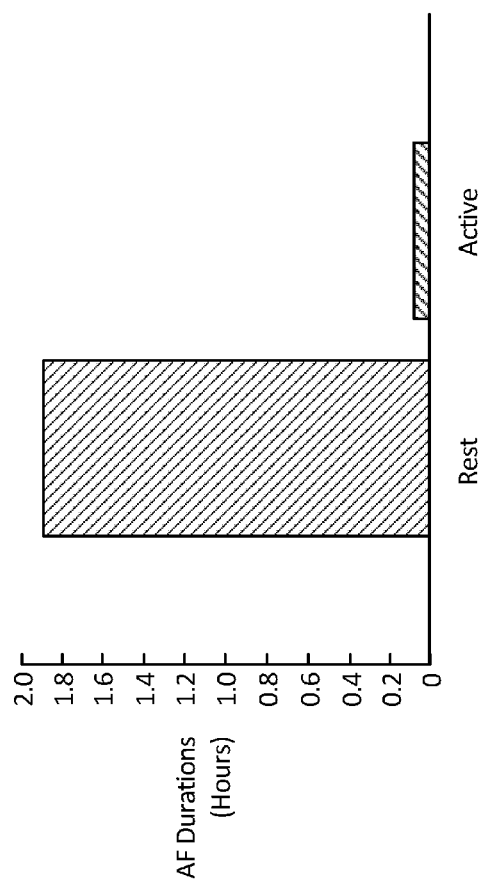

In the embodiment shown in FIG. 6A, the percentage of detected AF episodes occurring at night (between the hours of 10:00 PM and 8:00 AM) is approximately seventy percent, while the percentage of AF episodes occurring during the day (between the hours of 8:00 AM and 10:00 PM) is approximately thirty percent. In addition, FIG. 6B indicates that the percentage of detected AF episodes detected during periods of rest is approximately eighty percent, while the percentage of detected AF episodes detected during periods of activity is approximately twenty percent. The embodiment shown in FIG. 6C illustrates that the measured AF event durations (measured in hours) occurring at night is approximately 1.7 hours, while the measured AF event durations occurring during the day is approximately 0.2 hours. FIG. 6D illustrates that the measured AF event duration occurring during periods of rest is approximately 1.8 hours while the measured AF event duration occurring during periods of activity is approximately 0.1 hours.

Based on the information provided in FIGS. 6A-6D, which indicates that for this patient most occurrences of AF happen at night, while the patient is at rest, indicates that the etiology of the AF is likely cholinergic. This diagnosis may be provided directly to the physician for review and verification, or may be left entirely for the physician to diagnose based on the information provided and displayed.

FIGS. 7A-7D are bar charts provided as an output to a physician/doctor that illustrates graphically relationships between detected arrhythmias and patient state utilized to determine the etiology of the detected arrhythmia according to an embodiment of the present invention. The bar charts shown in FIGS. 7A-7D are organized the same way as the bar charts shown in FIGS. 5A-5D (and FIGS. 6A-6D), but are based on different data collected with respect to a different patient. In particular, FIGS. 7A-7D illustrate the benefit of relating AF episodes to activity level, and not simply to time of day measurements.

In the embodiment shown in FIG. 7A, the percentage of detected AF episodes occurring at night (between the hours of 10:00 PM and 8:00 AM) is approximately twenty-five percent, presumably while the patient is at rest. The percentage of AF episodes occurring during the day (between the hours of 8:00 AM and 10:00 PM) is approximately seventy-five percent, presumably when the patient is active. However, FIG. 7B indicates that the percentage of detected AF episodes detected during periods of rest is approximately eighty percent, while the percentage of detected AF episodes detected during periods of activity is only approximately twenty percent. This is counter to what would be expected based on the time of day measurements.

Figure 7C:
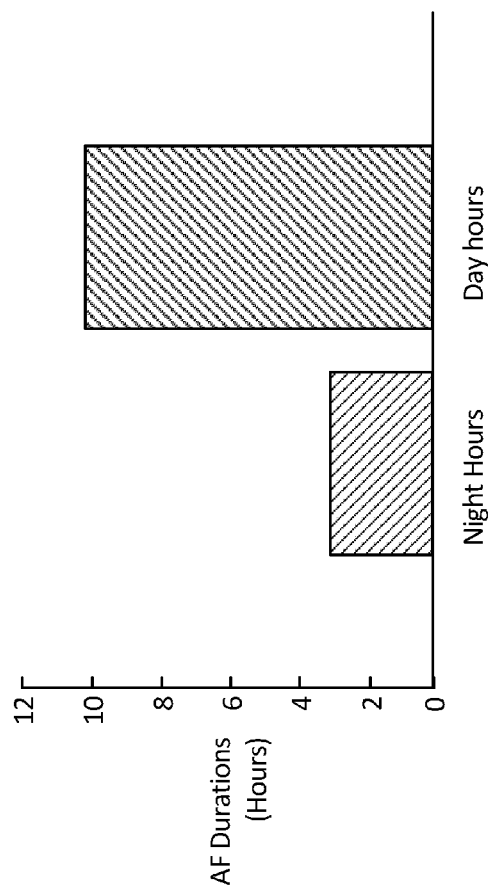
Figure 7D:
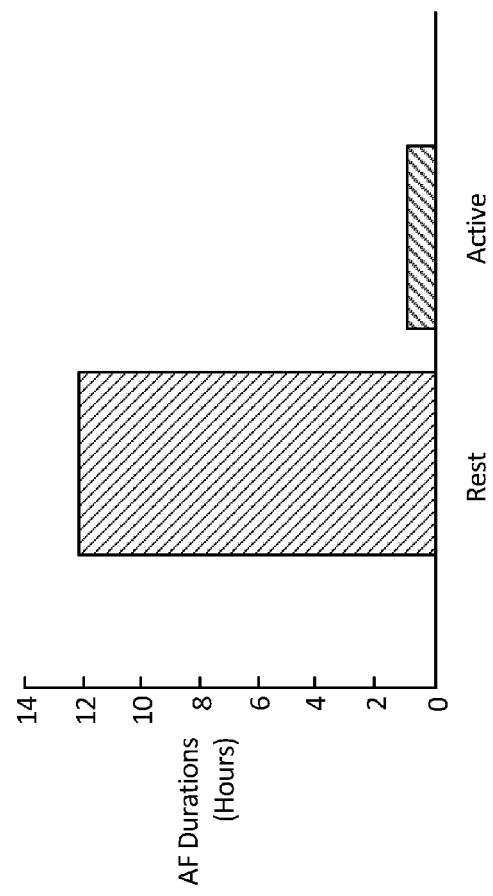

Similarly, the embodiment shown in FIG. 7C illustrates that the measured AF event durations (measured in hours) occurring at night is approximately 3 hours, presumably while the patient is at rest. Meanwhile, the measured AF event durations occurring during the day is approximately 10 hours, presumably while the patient is active. However, FIG. 7D illustrates that the measured AF event duration occurring during periods of rest is approximately 12 hours while the measured AF event duration occurring during periods of activity is only approximately 1 hour.

The information provided in FIGS. 7A-7D indicates that most occurrences of AF happen during the day, but while the patient is at rest. Therefore, even though the data indicates most AF events occur during the day, the correlation between the data indicates that the etiology of the AF is likely cholinergic because most of the occurrences of AF occur during periods of rest. The embodiment shown in FIGS. 7A-7D therefore illustrates the importance of correlating AF events to not only time of day but activity level in order to correctly determine the etiology of the detected arrhythmias. This diagnosis may be provided directly to the physician for review and verification, or may be left entirely for the physician to diagnose based on the information provided and displayed.

FIGS. 8A-8D are bar charts provided as an output to a physician/doctor that illustrates graphically relationships between detected arrhythmias and patient state utilized to determine the etiology of the detected arrhythmia according to another embodiment of the present invention. The bar charts shown in FIGS. 8A-8D are organized the same way as the bar charts shown in FIGS. 5A-5D, 6A-6D, and 7A-7D, but are based on different data collected with respect to a different patient. In particular, FIGS. 8A-8D illustrate the benefit of relating AF episodes to activity level, and not simply to time of day measurements for a different reason than that shown in FIGS. 7A-7D.

In the embodiment shown in FIG. 8A, the percentage of detected AF episodes occurring at night (between the hours of 10:00 PM and 8:00 AM) is approximately forty percent, presumably while the patient is at rest. The percentage of AF episodes occurring during the day (between the hours of 8:00 AM and 10:00 PM) is approximately sixty percent, presumably when the patient is active. In this embodiment, arrhythmic events are split relatively evenly between the times of day (nighttime, daytime), and therefore the results of this correlation are not definitive in any way. However, FIG. 8B indicates that the percentage of detected AF episodes detected during periods of rest is approximately seventy-five percent, while the percentage of detected AF episodes detected during periods of activity is only approximately twenty-five percent. That is, the correlation of detected arrhythmic events and activity level of the patient is much higher than the correlation between time of day and occurrence of arrhythmias.

The embodiment shown in FIG. 8C illustrates that the measured AF event durations (measured in hours) occurring at night is approximately three hours, presumably while the patient is at rest. Meanwhile, the measured AF event durations occurring during the day is approximately sixteen hours, presumably while the patient is active. This is in contrast with the correlation between percentage of arrhythmic events and time of day illustrated in FIG. 8A, which detected arrhythmic events relatively evenly across different times of day. However, FIG. 8D illustrates that the measured AF event duration occurring during periods of rest is approximately thirteen hours while the measured AF event duration occurring during periods of activity is only approximately five hours.

The information provided in FIGS. 8A-8D indicates that while the occurrences of AF are distributed throughout the day and night, because most of the occurrences happen while the patient is at rest, the etiology of the arrhythmic events is likely cholinergic. This diagnosis may be provided directly to the physician for review and verification, or may be left entirely for the physician to diagnose based on the information provided and displayed.

Figure 9:
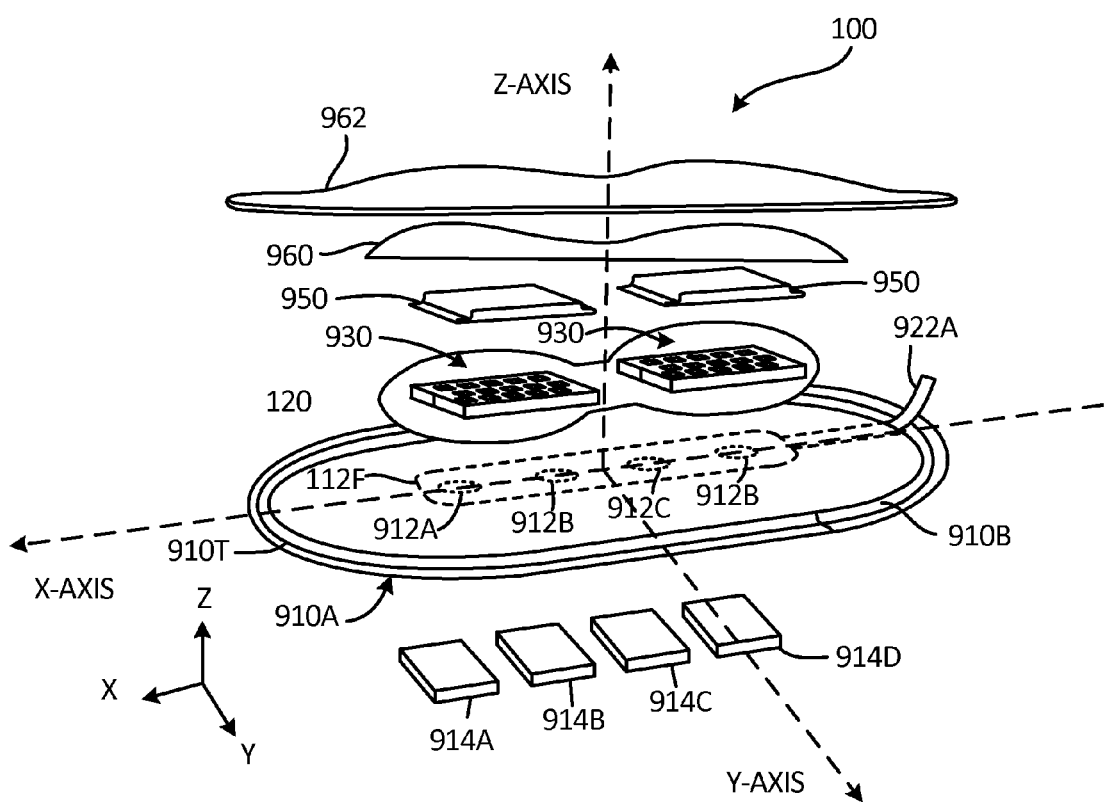
FIG. 9 shows an exploded view of an adherent device according to an embodiment of the present invention.

FIG. 9 is an exploded view, respectively, of embodiments of adherent device 100. In the embodiment shown in FIG. 9, adherent device includes adherent tape 910T, electrodes 912A, 912B, 912C, 912D with gels 914A, 914B, 914C, 914D, printed circuit board (PCB) 920, flexible connected 922A, electrical components/sensors 930 mounted on PCB 920, batteries 950, electronics housing cover 960, and flexible cover 962.

Adherent device 100 comprises at least two electrodes— although the embodiment shown in FIG. 9 includes electrodes 912A, 912B, 912C and 912D. Adherent device 100 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 100 comprises a first side, or a lower side 910A, that is oriented toward the skin of the patient when placed on the patient. The adherent patch 100 may also comprise a tape 910T which is a material, preferably breathable, with an adhesive (not shown) to adhere to patient P. Electrodes 912A, 912B, 912C and 912D are affixed to adherent patch 100. In many embodiments, at least four electrodes are attached to the patch. Gels 914A, 914B, 914C and 914D can each be positioned over electrodes 912A, 912B, 912C and 912D, respectively, to provide electrical conductivity between the electrodes and the skin of the patient. Adherent patch 100 also comprises a second side, or upper side 910B. In many embodiments, electrodes 912A, 912B, 912C and 912D extend from lower side 910A through adherent patch 100 to upper side 910B. An adhesive can be applied to upper side 910B to adhere structures, for example a breathable cover, to the patch such that the patch can support the electronics and other structures when the patch is adhered to the patient. In many embodiments, adherent patch 100 may comprise a layer of breathable tape 910T, for example a tricot-knit polyester fabric, to allow moisture vapor and air to circulate to and from the skin of the patient through the tape. Electrical signals received at electrodes 912A-912D may be communicated to electronic components 930 via flexible connection 922A, which is connected to PCB 920.

Electrical components 930 may include a processing module and/or other electrical components/sensors capable of monitoring and processing physiological parameters. In addition, electrical components 930 may include circuitry to transmit data to remote center 106 and receive commands from remote center 106. In many embodiments, electronics components 930 may comprise known low power circuitry, for example complementary metal oxide semiconductor (CMOS) circuitry components.

In one embodiment, electrical component 930 includes an activity sensor and activity circuitry that can comprise many known activity sensors and circuitry. In many embodiments, the accelerometer comprises at least one of a piezoelectric accelerometer, capacitive accelerometer or electromechanical accelerometer. The accelerometer can comprise a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example hydration data. In particular, 3D accelerometer may be utilized to determine an activity level of the patient, either alone or in combination with our monitored physiological parameters (e.g., heart rate, breath parameters, etc.).

In addition, electronic components 930 may utilize other types of sensors such as a temperature sensor, an activity sensor and activity circuitry, impedance circuitry and electrocardiogram circuitry. In some embodiments, electronic circuitry 930 may comprise a microphone and microphone circuitry to detect an audio signal, such as heart or respiratory sound, from within the patient. Electronic circuitry 930 may also include impedance circuitry (not shown) to generate both hydration data and respiration data. In many embodiments, impedance circuitry is electrically connected to electrodes 912A, 912B, 912C and 912D in a four pole configuration, such that electrodes 912A and 912D comprise outer electrodes that are driven with a current and comprise force electrodes that force the current through the tissue. The current delivered between electrodes 912A and 912D generates a measurable voltage between electrodes 912B and 912C, such that electrodes 912B and 912C comprise inner, sense, electrodes that sense and/or measure the voltage in response to the current from the force electrodes. In some embodiments, electrodes 912B and 912C may comprise force electrodes and electrodes 912A and 912D may comprise sense electrodes. The voltage measured by the sense electrodes can be used to measure the impedance of the patient and determine the respiration rate and/or hydration of the patient. In many embodiments, the impedance circuitry can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

In addition, electronic components 930 may include ECG circuitry utilized to generate electrocardiogram signals and data from two or more of electrodes 912A, 912B, 912C and 912D in many ways. In some embodiments, ECG circuitry (not shown) is connected to inner electrodes 912B and 912C, which may comprise sense electrodes of the impedance circuitry as described above. In many embodiments, the ECG circuitry may measure the ECG signal from electrodes 912A and 912D when current is not passed through electrodes 912A and 912D.

In addition, electronic circuitry 930 may comprise a processor module that can be configured to analyze physiological parameters monitored by adherent device 100 and to control collection and transmission of data from the impedance circuitry electrocardiogram circuitry and the accelerometer. In one embodiment, the processor module included as part of electronic circuitry 930 comprises a tangible medium, for example read only memory (ROM), electrically erasable programmable read only memory (EEPROM) and/or random access memory (RAM).

In many embodiments, electronics components 930 comprise wireless communications circuitry (not shown) to communicate with remote center 106. PCB 920 may comprise an antenna to facilitate wireless communication. The antenna may be integral with PCB 920 or may be separately coupled thereto. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

In this way, the disclosure provides a system and method of detecting atrial fibrillations and determining the etiology of detected atrial fibrillations (AFs). In particular, the disclosure describes how detected AF episodes are associated with an activity level of the patient to determine the etiology of the detected AF episodes. A benefit of the system and method described herein, is that it does not require a patient to be present in the physician's office to collect the data. Rather, the patient wears the device for an extended period of time, and data is collected as the patient undergoes normal day to day activities, including periods of rest and periods of activity. In addition, the system and method described herein prevents the physician/doctor from having to review ALL data collected over the period of time the patient wears the adherent/implantable device. For example, as described with respect to FIGS. 2A-2C, the adherent device may be configured to collect a sample of ECG strips that are communicated to a physician/doctor for review and verification, but will not collect/transmit all detected ECG strips including AF episodes. In addition, the report generated by adherent/implantable device provides a concise summary of relationships detected between detected AF episodes and other physiological parameters such as activity level, without requiring the data be parsed by the physician/doctor. This provides considerable time-savings to health care providers, without sacrificing quality of the care provided.

Discussion of Possible Embodiments

The following are non-exclusive descriptions of possible embodiments of the present invention.

A method of detecting and classifying atrial fibrillations (AFs) may include monitoring an electro-cardiogram (ECG) signal of the patient and detecting atrial fibrillation (AF) episodes based on the monitored ECG signal. In addition, the method may include monitoring one or more physiological parameters to determine an activity level of the patient, and may further include associating a detected AF episode with an activity level of the patient at a time of the detected arrhythmia. The method may further include classifying a cause of the detected AF episodes as adrenergic if detected AF episodes occur when the patient is active and classifying the cause of the detected AF episodes as vagal if detected AF episodes occur when the patient is at rest. The method may further include generating a report regarding the determined classification of the AF episodes.

The method of the preceding paragraph can optionally include, additionally and/or alternatively any, one or more of the following features, configurations and/or additional components.

The method may include monitoring of the ECG signal and detection of AF episodes for a prescribed monitoring period.

The method may further include incrementing a count of active AF episodes detected within the prescribed monitoring period in response to AF episodes detected during a period of patient activity, and may include incrementing a count of resting AF episodes detected within the prescribed monitoring period in response to AF episodes detected during a period of patient rest.

The method may further include classifying a cause of the detected AF episodes as adrenergic or vagal based on the count of active AF episodes and the count of resting episodes detected within the prescribed monitoring period.

The method may further include communicating an ECG strip collected during a detected AF episode to a remote center for verification, wherein only ECG strips representing verified AF episodes are retained.

The method may further include including verified AF episodes in the generated report regarding the determined classification of the AF episodes.

The method may further include communicating up to a maximum number of ECG strips collected during AF episodes to the remote center for verification, wherein once the maximum number of ECG strips representing AF episodes have been communicated and verified, no additional ECG strips are communicated to the remote center.

The method may further include capturing additional physiological parameters associated with the patient with respect to a detected AF episode for inclusion in the generated report.

In another embodiment, an adherent device is utilized to determine the etiology of detected AF episodes as either adrenergic or vagal. The adherent device may include a plurality of electrodes and sensing circuitry, an activity sensor, and a processing module. The plurality of electrodes and sensing circuitry may be utilized to monitor an electro-cardiogram (ECG) signal of the patient to which the adherent device is affixed. The activity may be utilized to detect an activity level of the patient. The processing module may be configured to receive the monitored ECG signal and the monitored activity level. In response, the processing module may detect atrial fibrillation episodes based on the monitored ECG signal and associate with each detected AF episode an activity level monitored at the time of the AF episode, wherein the processing module may additionally maintains data related to detected AF episodes and activity level associated with the detected AF episodes. In response detected AF episodes and activity levels, the processing module may classify an etiology of the detected AF episodes as adrenergic or vagal.

The adherent device of the preceding paragraph can optionally include, additionally and/or alternatively any, one or more of the following features, configurations and/or additional components.

The adherent device may further include wherein data maintained by the processing module includes a count of AF episodes that occur during periods of patient rest and a count of AF episodes that occur during periods of patient activity.

The adherent device may further include wherein data maintained by the processing module includes a total duration of AF episodes that occur during periods of patient rest and a total duration of AF episodes that occur during periods of patient activity.

The adherent device may further include wherein in response to a detected AF episode, the processing module communicates an ECG strip including information related to the detected AF episode to a remote center for review and verification of the detected AF episode.

The adherent device may further include wherein during a monitoring period, a maximum number of ECG strips are communicated to the remote center for review, wherein after the maximum number of ECG strips have been communicated and verified, subsequent AF episodes are utilized to update maintained data but are not communicated to the remote center for verification.

The adherent device may further include wherein the processing module generates a report that includes at most a maximum number of ECG strips, a count of resting AF episodes that occurred during the monitoring period, and a count of active AF episodes that occurred during the monitoring period.

The report generated by the processing module may further include one or more of time of day, patient posture, respiration rate as compared with resting AF episodes and active AF episodes.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of detecting and classifying atrial fibrillations (AFs), the method comprising:
   monitoring an electro-cardiogram (ECG) signal of a patient for a prescribed monitoring period;
   detecting atrial fibrillation (AF) episodes during the prescribed monitoring period based on the monitored ECG signal;
   monitoring one or more physiological parameters to determine an activity level of the patient during the prescribed monitoring period;
   associating a detected AF episode with the determined activity level of the patient at a time of the detected arrhythmia;
   for each detected AF episode, incrementing a count of active AF episodes detected within the prescribed monitoring period if the AF episode is associated with a period of patient activity and incrementing a count of resting AF episodes detected within the prescribed monitoring period if the AF episode is associated with a period of patient rest;
   classifying a cause of the detected AF episodes based, at least in part, on the count of resting AF episodes and the count of active AF episodes, wherein the cause of the detected AF episodes is classified as adrenergic if the count of active AF episodes indicates AF episodes occur when the patient is active and wherein the cause of the detected AF episodes is identified as vagal if the count of resting AF episodes indicates AF episodes occur when the patient is at rest; and generating a report regarding the classified causes of the AF episodes, wherein the report includes the count of resting AF episodes and the count of active AF episodes.

2. The method of claim 1, wherein in response to a detected AF episode during a period of patient activity, an ECG strip representing the detected AF episode is communicated to a remote center for verification and retention of the ECG strip representing the detected AF episode if verified.

3. The method of claim 2, wherein verified AF episodes are included in the generated report regarding the determined classification of the AF episodes.

4. The method of claim 2, wherein ECG strips representing AF episodes are communicated to the remote center for verification, wherein once a determined number of ECG strips representing AF episodes have been communicated and verified, no additional ECG strips are communicated to the remote center.

5. The method of claim 1, further including capturing additional physiological parameters associated with the patient with respect to a detected AF episode for inclusion in the generated report.

6. The method of claim 1, further including:
measuring a duration of a detected AF episode;
for each detected AF episode, adding the duration of the detected AF episode to a total active AF burden/duration in response to the detected AF episode being associated with a period of patient activity and adding the duration of the detected AF episode to a total resting AF burden/duration in response to the detected AF episode being associated with a period of patient rest; and
wherein classifying a cause of the detected AF episodes is further based on the total active AF burden/duration and the total resting AF burden/duration.

7. An adherent device adapted to be affixed to a patient, the adherent device comprising:
a plurality of electrodes and sensing circuitry configured to monitor an electrocardiogram (ECG) signal of the patient;
an activity sensor configured to monitor an activity level of the patient; and
a processing module configured to receive the monitored ECG signal and the monitored activity level, wherein the processing module is configured to detect atrial fibrillation (AF) episodes based on the monitored ECG signal and associate with each detected AF episode an activity level monitored at a time of the AF episode, wherein the processing module is configured to increment a count of active AF episodes detected within a prescribed monitoring period in response to the detected AF episode being associated with a period of patient activity and increment a count of resting AF episodes detected within the prescribed monitoring period in response to the detected AF episode being associated with a period of patient rest, wherein the processing module is configured to classify an etiology of the detected AF episodes as adrenergic or vagal based, at least in part, on the count of active AF episodes and the count of resting AF episodes.

8. The adherent device of claim 7, wherein the processing module is configured to measure a duration of each detected AF episode and for each detected AF episode, add the duration of the detected AF episode to a total active AF burden/duration in response to the detected AF episode being associated with a period of patient activity and add the duration of the detected AF episode to a total resting AF burden/duration in response to the detected AF episode being associated with a period of patient rest, wherein classifying the etiology of the detected AF episodes as adrenergic or vagal is based, at least in part, on the total resting AF burden/duration and the total active AF burden/duration.

9. The adherent device of claim 7, wherein the processing module is configured to communicate an ECG strip including information related to the detected AF episode to a remote center for review and verification of the detected AF episode.

10. The adherent device of claim 9, wherein the processing module is configured to increment a count of active ECG strips in response to the remote monitoring center verifying a detected active AF episode and to increment a count of resting ECG strips in response to the remote monitoring center verifying a detected resting AF episode, wherein the processing module is configured to discontinue communicating ECG strips related to active AF episodes when the count of active ECG strips reaches an active ECG strip threshold, and discontinues communicating ECG strips related to resting AF episodes when the count of resting ECG strips reaches a resting ECG strip threshold.

11. The adherent device of claim 10, wherein the processing module is configured to generate a report that includes ECG strips communicated from the processing module, the count of resting AF episodes that occurred during a monitoring period, and the count of active AF episodes that occurred during a monitoring period.

12. The adherent device of claim 11, wherein the processing module further includes in the generated report one or more of time of day, patient posture, and respiration rate associated with resting AF episodes and active AF episodes.

13. A method of detecting and classifying atrial fibrillations (AFs), the method comprising:
monitoring an electro-cardiogram (ECG) signal of a patient for a prescribed monitoring period;
detecting atrial fibrillation (AF) episodes based on the monitored ECG signal during the prescribed monitoring period;
measuring a duration of each AF episode detected during the prescribed monitoring period;
monitoring one or more physiological parameters to determine an activity level of the patient during the prescribed monitoring period;
associating a detected AF episode with the determined activity level of the patient at a time of the detected arrhythmia;
for each detected AF episode, adding the duration of the detected AF episode to a total active AF duration if the AF episodes is associated with a period of patient activity and to a total resting AF duration if the AF episode is associated with a period of patient rest; and
classifying a cause of the detected AF episodes based, at least in part, on the total active AF duration and the total resting AF duration, wherein the cause of the detected AF episodes is identified as adrenergic if the total active AF duration indicates AF episodes occur when the patient is active, and wherein the cause of the detected AF episodes is identified as vagal if the total resting AF duration is indicates AF episodes occur when the patient is at rest.

14. The method of claim 13, wherein a count of active AF episodes is incremented if the AF episodes is associated with a period of patient activity, and wherein a count of resting AF episodes is incremented if the AF episodes is associated with a period of patient rest.

15. The method of claim 14, further comprising generating a report regarding the classified causes of the AF episodes, wherein the report includes the total duration of resting AF episodes, the total duration of active AF episodes, the count of active AF episodes, and the count of resting AF episodes.

* * * * *